United States Patent
Dechelette et al.

(10) Patent No.: US 9,101,785 B2
(45) Date of Patent: Aug. 11, 2015

(54) USE OF 2,3-DIHYDROXYPROPYL DODECANOATE FOR TREATING SEBORRHOEA

(75) Inventors: Corinne Dechelette, Rabastens (FR); Redoules Daniel, Toulouse (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 13/516,347

(22) PCT Filed: Dec. 17, 2010

(86) PCT No.: PCT/EP2010/070028
§ 371 (c)(1), (2), (4) Date: Jun. 15, 2012

(87) PCT Pub. No.: WO2011/073370
PCT Pub. Date: Jun. 23, 2011

(65) Prior Publication Data
US 2012/0258065 A1    Oct. 11, 2012

(30) Foreign Application Priority Data
Dec. 18, 2009 (FR) .................................... 09 59165

(51) Int. Cl.
A61Q 19/00 (2006.01)
A61K 8/37 (2006.01)

(52) U.S. Cl.
CPC ............... *A61Q 19/008* (2013.01); *A61K 8/375* (2013.01)

(58) Field of Classification Search
None
See application file for complete search history.

(56) References Cited

U.S. PATENT DOCUMENTS

| | | | |
|---|---|---|---|
| 4,921,694 A | | 5/1990 | Hoppe et al. |
| 5,057,501 A | * | 10/1991 | Thornfeldt ..................... 514/53 |
| 5,550,145 A | * | 8/1996 | Olund et al. .................. 514/396 |
| 6,110,908 A | * | 8/2000 | Guthery ........................ 514/188 |
| 6,126,947 A | * | 10/2000 | Savion et al. ................. 424/401 |
| 2005/0008711 A1 | * | 1/2005 | Di Pierro ...................... 424/727 |
| 2009/0203628 A1 | | 8/2009 | Marini |

FOREIGN PATENT DOCUMENTS

FR    2 867 973 A1    9/2005

OTHER PUBLICATIONS

International Search Report issued in PCT/EP2010/070028 on May 23, 2012.
Luu-The et al., "Characterization, Expression, and immunohistochemical Localization of 5α-Reductase in Human Skin", J Invest Dermatol, vol. 102 (1994) pp. 221-226.
Niederprüm et al., "inhibition of Steroid 5α-Reductase Activity by Aliphatic Fatty Acids Candidates for Chemoprevention of Prostate Cancer", Animals of the NY Academy of Sciences, NY, NY, vol. 768 (1995) pp. 227-230.

* cited by examiner

*Primary Examiner* — Michael B Pallay
(74) *Attorney, Agent, or Firm* — Birch, Stewart, Kolasch & Birch, LLP

(57) ABSTRACT

Disclosed is a method of treating seborrhoea by administering to an patient in need thereof a therapeutically effective amount of 2,3-dihydroxypropyl dodecanoate. In particular, the seborrhoea is associated with the skin, including the scalp. The method topically applies a composition containing a therapeutically effective amount of 2,3-dihydroxypropyl dodecanoate to the skin.

4 Claims, 1 Drawing Sheet

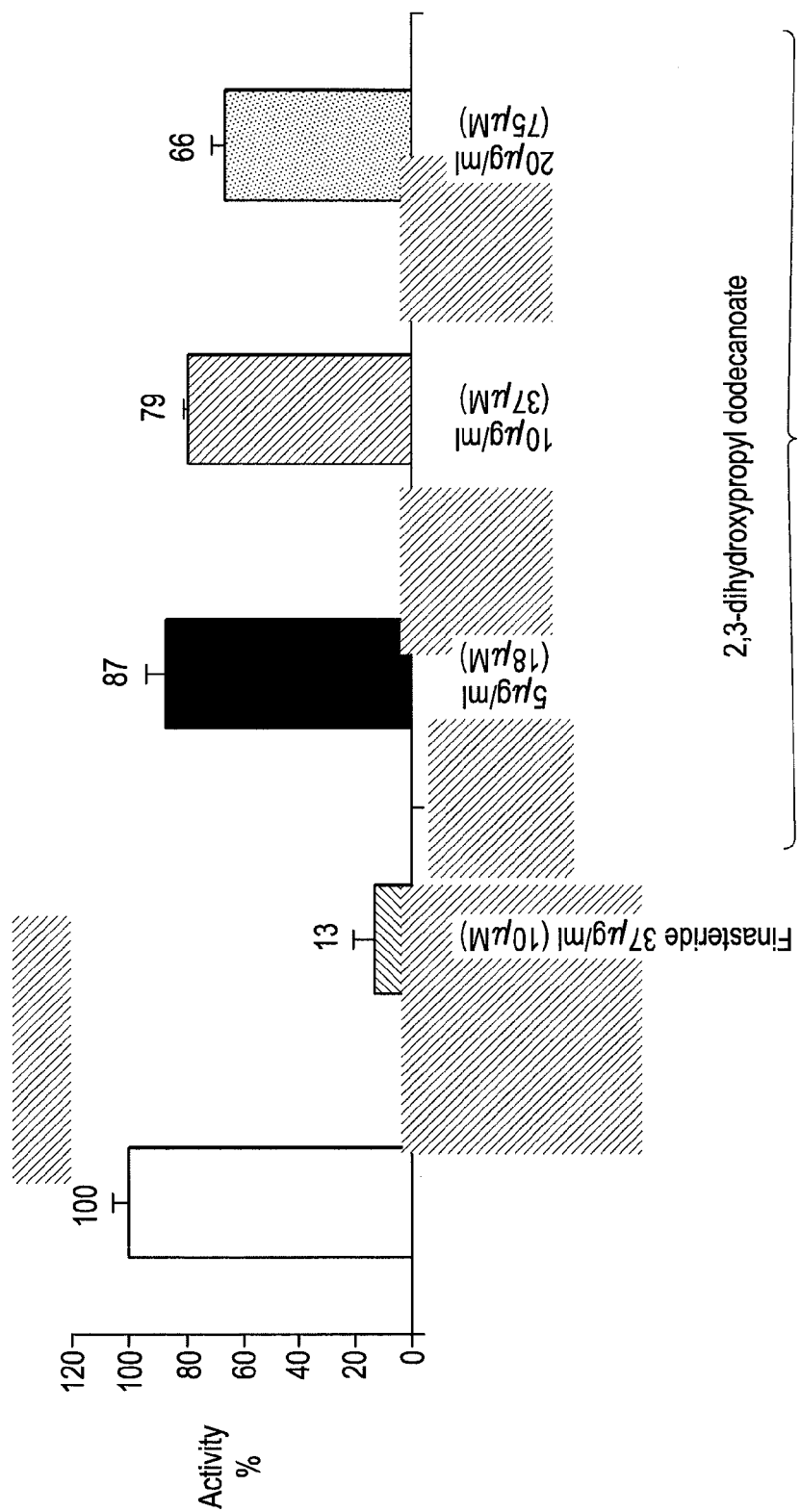

USE OF 2,3-DIHYDROXYPROPYL DODECANOATE FOR TREATING SEBORRHOEA

The present invention relates to 2,3-dihydroxypropyl dodecanoate for the use thereof for treating seborrhoea. The seborrhoea may be associated with the skin or scalp.

The invention also relates to cosmetic compositions comprising 2,3-dihydroxypropyl dodecanoate for treating seborrhoea.

Sebum is the secretion, by the sebaceous glands of the skin, of a lipid film which serves to protect the skin and, combined with sweat, protects the skin against drying.

Sebum enables waterproofing of the skin and plays a role in the development of the epidermal structure.

It protects the skin from micro-organisms by acidification (presence of lactic acid and fatty acids) and provides a degree of waterproofing. It enables the skin to be supple and plays a role in epidermal growth.

It is also found on hair on the body and head.

Sebum is produced by the sebaceous glands.

Overall, humans have 2,000,000 sebaceous glands attached to 6,000,000 hairs on the body and head.

Sebaceous gland distribution is not uniform. Sebaceous gland density reaches 300 to 900 sebaceous glands/cm$^2$ on the face and scalp, and this density is in the region of 100 sebaceous glands/cm$^2$ in the upper chest and back.

The sebaceous gland has a holocrine mode of secretion, i.e. complete cell elimination. The secretory portion thereof is alveolar.

Seborrhoea consists of excessive sebum production by the sebaceous glands.

Seborrhoea may have various causes:
Nervous system: emotional stress, nervous tension exacerbating the sebaceous function,
Fatigue,
Unbalanced diet,
Some medication (psychotropic drugs),
Unsuitable cosmetic treatments "stripping" the skin and/or scalp, and triggering reactive seborrhoea,
The main cause is hormonal: the sebaceous gland is hormone-dependent and the activity thereof is influenced by androgens. Androgens are only active under the influence of 5-α reductase enzyme which metabolises androgens in the sebaceous gland, inducing sebum production. Hyperactivation of 5-α reductase enzyme causes seborrhoea.

Signs of seborrhoea are found in the middle face region (forehead, nose, chin) where sebaceous glands are the most abundant and largest. Seborrhoea also appears on the scalp where it is predominant in the frontal and frontotemporal regions and at the top of the head.

Seborrhoea causes aesthetic problems. In the case of skin, the skin exhibits a shiny appearance, the complexion is dull and the openings of the hair follicles are dilated. Furthermore, makeup does not hold well on this so-called greasy skin type.

In the case of seborrhoea of the scalp, hair appears greasy and dull and is difficult to style. In the case of intense seborrhoea, it is referred to as oily, moist and may be associated with a rancid odour.

In order to treat seborrhoea and remedy the aesthetic problems associated with seborrhoea, it was surprisingly demonstrated that using 2,3-dihydroxypropyl dodecanoate makes it possible to inhibit 5-α reductase enzyme activity and thus reduce sebum secretion.

1) 2,3-dihydroxypropyl dodecanoate:

2,3-dihydroxypropyl dodecanoate (Formula 1), also referred to as glyceryl laurate or glyceryl monolaurate, is an ester formed from lauric acid and glycerol having the chemical formula $C_{15}H_{30}O_4$. It is usually used as an emulsifier such as for example in household cleaning products, but also in some food products.

Formula 1: 2,3-dihydroxypropyl dodecanoate

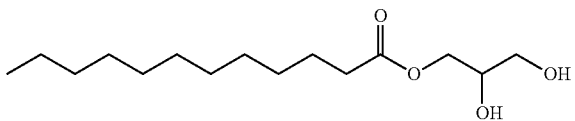

2) 5-α reductase enzyme

There are two isozymes of 5-α reductase enzyme: 5-α reductase 1 and 5-α reductase 2. Type 1 is essentially expressed in the skin, located in the sebaceous gland and the dermal papilla and is active at pH 7, whereas type 2 is expressed in the prostate and is active at pH 5 (Luu-The et al, Characterization, Expression and Immunohistochemical localization of 5-alpha reductase in human skin, The Journal of Investigate Dermatology, p 221-226, 1994).

5-α reductase enzyme is an enzyme involved in the steroid metabolism (Luu-The et al, Characterization, Expression and Immunohistochemical localization of 5-alpha reductase in human skin, The Journal of Investigate Dermatology, p 221-226, 1994).

More specifically, this enzyme reduces the Δ4,5 bond of testosterone (Formula 2), producing dihydrotestosterone (androstanolone) (DHT) (Formula 3) is also an androgen hormone.

The sebaceous gland is hormone-dependent, and the function thereof is linked with testosterone. Testosterone is produced by the testicles, ovaries (androstenedione) and the adrenals (dehydroepiandrosterone). In target cells, testosterone is converted into active DHT by 5-α reductase enzyme. After combining with a cytosolic receptor, DHT binds on a nuclear receptor and induces the synthesis of proteins responsible for sebum production.

Formula 2: Testosterone

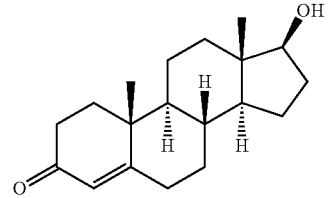

Formula 3: Dihydrotestosterone (DHT)

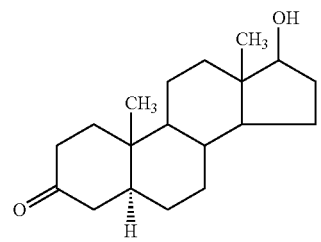

Seborrhoea is linked with 5-α reductase enzyme hyperactivity associated with an increase in the number of cytosolic receptors.

Inhibiting 5-α reductase enzyme activity thus makes it possible to reduce androgen metabolisation and thus sebum production.

3) Biological results: Inhibition of 5-α reductase activity with 2,3-dihydroxypropyl dodecanoate:

Protocol:

Biological Model:

Cell type: Normal human dermal fibroblasts (NHDF).

Culture conditions: 37° C., 5% $CO_2$.

Culture medium: DMEM supplemented with 2 mM of L-glutamine, 50 U/ml of penicillin, 50 μg/ml of streptomycin, 10% foetal calf serum.

Test culture medium: DMEM supplemented with 2 mM of L-glutamine, 50 U/ml of penicillin, 50 μg/ml of streptomycin and 1% foetal calf serum.

Radiolabelled testosterone: [4-14C]testosterone (Amersham). Radiolabelled testosterone was dissolved in ethanol and diluted in the test culture medium.

Test Compound:

Test compound: 2,3-dihydroxypropyl dodecanoate.

Positive control: finasteride.

Finasteride is well known for inhibiting 5-α reductase activity and thus preventing the metabolisation of testosterone to DHT.

Control: ethanol, which has no 5-α reductase inhibition activity.

Cell Culture and Treatment:

The fibroblasts were cultured to confluence. The culture medium was then removed and replaced by the test culture medium containing or free from the test compound, the positive control or control and the cells were pre-incubated for 24 hours. After incubation, the cells were treated with the test compound or the negative control and the radiolabelled testosterone was added. The cells were then incubated for 24 hours. All the experiments were conducted three times.

Extractions and Analyses:

The steroids were extracted from the supernatants with two volumes of chloroform/methanol and dried. The various molecular entities (testosterone metabolites) were separated by thin layer chromatography on silica plates (RE/silica, Whatman) in a solvent mixture comprising dichloromethane, ethyl acetate and methanol.

The plates were autoradiographed and the testosterone metabolites were quantified using a phosphorImager which is a beta radiation detector and specific software (Packard Instrument).

The decrease in the quantity of radiolabelled DHT detected is a sign of 5-α reductase enzyme activity.

Data Processing:

The raw data were analysed with Microsoft Excel® software.

Calculation of standard error of the mean=standard deviation/ $\sqrt{}$ (n)

Viability=(Optical density of sample/Optical density of control)×100

The results are expressed in FIG. 1 appended illustrating the effect of 2,3-dihydroxypropyl dodecanoate on DHT production by human fibroblasts.

It is observed that the ethanol control has no effect on testosterone metabolisation and thus does not inhibit 5-α reductase activity.

The positive control, finasteride, tested at 10 μM, lowers testosterone metabolisation to DHT significantly and thus inhibits 5-α reductase activity.

In the case of 2,3-dihydroxypropyl dodecanoate, inhibition of 5-α reductase activity is also observed. Furthermore, a dose-effect of this inhibition is observed: for 75 μM of 2,3-dihydroxypropyl dodecanoate, the 5-α reductase enzyme activity is reduced to 66%.

These results demonstrate that 2,3-dihydroxypropyl dodecanoate indeed inhibits 5-α reductase enzyme activity.

One aim of the invention is thus that of using 2,3-dihydroxypropyl dodecanoate for treating seborrhoea, preferentially seborrhoea of the skin or scalp. The present invention relates to the use of 2,3-dihydroxypropyl dodecanoate as a sebomattifying cosmetic agent.

Seborrhoea is frequently associated with androgenetic alopecia. Alopecia is defined as partial or total hair loss. The lifetime of a hair is subject to a cycle known as the piliary cycle including three successive phases. The anagen phase is a period of active and continuous growth, associated with intense metabolic activity at root level. During the catagen phase, mitotic activities slow down. The hair undergoes involution, the follicle is stunted and the dermal implantation thereof appears at an increasingly high level. The final phase is the telogen phase consisting of a follicle resting phase and the hair eventually falls out, pushed by a new hair. The piliary cycle is complete, another one can commence. There are approximately 20 to 25 cycles per root lifetime in humans. In the course of ageing, hairs become finer and their life cycles shorter.

In this way, hereditary androgenic alopecia (formerly known as seborrhoeic alopecia) is the most common form of alopecia and affects approximately 70% of men. A hair with a shorter life cycle is the primary characteristic of androgenetic alopecia. All the other symptoms are merely consequences of this shorter life cycle. Initially, the problem caused by this form of alopecia stems from the fact that androgens speed up the anagen phase, forcing the hair to move too quickly to the telogen phase and not allowing the hair follicle enough time to produce high-quality keratin. A vicious circle then occurs: the quicker the hair is produced, the sooner it falls out and the quicker the cycles succeed each other, each time producing a weaker and shorter hair than the previous one. Eventually, the stock of renewal cycles is exhausted, the follicle no longer produces anything and dies. This form of alopecia due to excess androgens also affects women during menopause or following androgen treatment. It starts at the temples and the crown.

Consequently, lowering 5-α reductase enzyme activity should inhibit seborrhoea and thus slow down hair loss.

4) Composition

The present invention also relates to cosmetic compositions comprising 2,3-dihydroxypropyl dodecanoate for treating seborrhoea. In particular, the present invention relates to cosmetic compositions comprising 2,3-dihydroxypropyl dodecanoate for treating seborrhoea of the skin or scalp. The subject matter of the invention also consists of a method for the cosmetic treatment of seborrhoea comprising the application on the skin or scalp of a cosmetic composition according to the present invention. In particular, it may consist of a method for the cosmetic treatment of seborrhoea of the skin or scalp.

According to the invention, the cosmetic composition may comprise 0.01 to 20% and preferably 0.5 to 10% and more specifically 1 to 5% by weight with respect to the total weight of the composition of 2,3-dihydroxypropyl dodecanoate.

According to a further embodiment of the invention, the cosmetic composition is that further comprising Avène thermal spring water.

The composition of Avène thermal spring water is as follows:

| Composition of Avène Thermal Spring Water | mg/ml |
|---|---|
| Chlorides | 5.4 |
| Bicarbonates | 226.7 |
| Sulphates | 13.1 |
| Silica | 14 |
| Calcium | 42.7 |
| Magnesium | 21.2 |
| Sodium | 4.8 |
| Potassium | 0.8 |
| Iron | 0.005 |
| Selenium | 0.005 |
| Zinc | 0.02 |
| Copper | 0.005 |
| Dry residue | 207 |
| Mineralisation | Low |
| pH | 7.5 |
| Osmolarity | Hypotonic |

A further embodiment of the invention is the cosmetic composition wherein 2,3-dihydroxypropyl dodecanoate is the only active ingredient.

According to the invention, the cosmetic composition is that comprising 2,3-dihydroxypropyl dodecanoate, Avène thermal spring water and a cosmetically acceptable substrate.

The term "cosmetically acceptable substrate" refers to any adjuvant or excipient suitable for the manufacture, storage or administration of the cosmetic composition.

The composition according to the invention may be in any of the forms normally used for topical application, particularly in hydroalcoholic form, in the form of an oil-in-water or water-in-oil or multiple emulsion, an oily gel, or a liquid, pasty or solid anhydrous product or in the form of a dispersion in the presence of spherules. These compositions are prepared using routine methods.

The composition may be in any suitable dosage form. The composition may be in the form of an aqueous, alcoholic, hydroalcoholic or oily solution, a lotion or serum type dispersion, a suspension, microcapsules or microparticles; ionic and/or non-ionic vesicular dispersions, an aqueous, oily lotion or in serum form; a foam, a solid preparation, e.g. a stick; an aerosol composition also comprising a pressurised propellant, a gel or in patch form.

This composition may have a variable fluidity and have the appearance of white or coloured cream, ointment, milk, or paste. It may optionally be applied onto the skin or hair in aerosol form.

The composition according to the invention may be in the form of a hair care composition, particularly a shampoo, setting lotion, styling lotion, cream or gel, dye composition or anti-hair loss gel.

It may also be in the form of a facial or body cleansing, protection or care composition (e.g. day cream, night cream, make-up removal cream, protective or treating body lotions, skin care lotion, gel or foam), a make-up composition such as foundation.

If the composition is an emulsion, the proportion of the fat phase may range from 5% to 80% by weight, and preferably from 5% to 50% by weight with respect to the total weight of the composition. The oils, waxes, emulsifiers and co-emulsifiers used in the composition in emulsion form are chosen from those conventionally used in the field of cosmetics.

—Fat Phases:

The term fat phase refers to lipophilic compounds such as oils, gums, pastes and waxes.

The oils are preferably chosen from plant oils, animal oils, mineral oils, synthetic oils, silicone oils, liquid fatty acid esters, liquid fatty acids and liquid fatty amides.

Examples of plant oils particularly include sweet almond oil, avocado oil, castor oil, olive oil, jojoba liquid wax, sunflower oil, wheat germ oil, sesame oil, peanut oil, grape seed oil, soybean oil, rapeseed oil, safflower oil, coconut oil, corn oil, hazelnut oil, apricot kernel oil and calophyllum oil.

Perhydrosqualene can particularly be cited as an example of an animal oil.

Examples of synthetic oil particularly include squalene, poly($\alpha$-olefins) such as isododecane or isohexadecane, transesterified plant oils and fluorinated oils.

Examples of silicone oils include cyclic polydimethylsiloxane (INCI name: cyclomethicone) such as decamethyl pentasiloxane and low-viscosity linear polymethylsiloxanes.

Waxes suitable for use in the present invention are, for example, waxes of animal, plant, mineral or synthetic origin, such as beeswax, spermaceti, fluorinated or perfluorinated waxes, lanolin waxes, Candellila, Ouricury, Carnauba, Japan, cocoa butter waxes, cork fibre or sugar cane waxes, rice bran wax, pine wax, cotton wax; microcrystalline waxes, paraffin wax, petrolatum, petroleum jelly, ozokerie, montan wax, hydrogenated oils having a temperature above 40° C. such as hydrogenated jojoba oil, polyethylene waxes and the waxes obtained by Fischer-Tropsch synthesis.

The waxes may also be chosen from waxy fatty alcohols and waxy fatty esters.

Waxy fatty acid esters are fatty acid esters, i.e. carboxylic acid esters comprising at least 10 carbon atoms and a monoalcohol or a polyol. The waxy fatty acid esters suitable for use in the composition according to the invention may be mono, di, or triesters. Examples of waxy esters include myristyl myristate and stearyl stearate.

The waxy fatty acids suitable for use in the composition according to the invention preferably comprise 12 to 24 carbon atoms and may be saturated or unsaturated, optionally branched, and comprise one or a plurality of hydroxy functions. Examples include lauric acid, stearic acid, cetylic acid and behenic acid.

Examples of waxy amides include ceramides such as n-oleyldihydrosphingosine.

—Emulsifiers:

Emulsifiers enable easier dispersion of two mutually insoluble phases. The emulsifier and the co-emulsifier are present in the composition in a proportion ranging from 0.3% to 30% and preferably from 0.5 to 20% and preferentially from 0.5 to 10% by weight with respect to the total weight of the composition.

The emulsifying system may particularly comprise one or a plurality of compounds chosen from ethoxylated fatty alcohols, fatty acid and PEG esters, ethoxylated fatty acid partial glycerides, polyglycerol fatty acid triglycerides and the ethoxylated derivatives thereof.

Ethoxylated fatty acid alcohols according to the invention include ethylene oxide addition products with behenyl alcohol, particularly those comprising 6 to 12 oxyethylenated groups (for example Beheneth-9 or Behenth-10); ethylene oxide addition products with stearyl alcohol, particularly those comprising 6 to 12 oxyethylenated groups (for example steareth-9); ethylene oxide addition products with isostearyl alcohol, for example those comprising 6 to 12 oxyethylenated groups (Isosteareth-9), and mixtures thereof.

Non-ionic surfactants also include different oxyethylenated fatty alcohols to those described above, i.e. ethylene oxide addition products with lauryl alcohol (laureth-9 to laureth-50); ethylene oxide addition products with cetearyl or cetyl stearyl alcohol (Ceteareth-9 to Ceteareth-30), ethylene oxide addition products with cetyl alcohol (Ceteth-9 to Ceteth-30); and mixtures thereof.

Additional surfactants may also be included in the composition. These additional surfactants may be fatty acid salts having 8 to 30 carbon atoms, such as palmitic acid salts, stearic acid, behenic acid, glycerol fatty esters, such as glyceryl stearate; oxyethylenated derivatives of fatty acid salts and glycerol fatty esters comprising 2 to 8 ethylene oxide groups and mixtures thereof, and any emulsifier and conditioning agent known to those skilled in the art.

—Preservatives:

Preservatives are present in the composition in the proportion ranging from 0.1% to 5% and preferably from 0.1% to 1% by weight with respect to the total weight of the composition.

The composition may further comprise antimicrobial agents such as preservatives or antifungal agents chosen from alcohols, suitable for containing one or a plurality of aromatic substituents, for example phenoxyethanols such as 2-phenoxyethanol, 1-phenoxy-2-propanol, benzyl alcohol, 2-hydroxybiphenyl, parabens, such as methylparaben, ethylparaben, propylparaben, butylparaben, isobutylparaben, sodium methylparaben, sodium ethylparaben, sodium propylparaben, sodium isobutylparaben, sodium butylparaben or sodium isobutylparaben, imidazolidinyl urea, diazolidinyl urea, sodium hydroxymethylglycinate, halogenated derivatives such as iodopropynyl butylcarbamate, 2-bromo-2-nitropropan-1,3-diol, 2,4,4'-trichloro-2'-hydroxydiphenylether (triclosan), 3,4,4'-trichlorocarbanilide (triclocarban), chlorbutanulum, 2,4-dichlorobenzyl alcohol, N-(4-chlorophenyl-N'-(3,4-dichlorophenyl urea, 1,2-dibromo-2, 4-dicyanobutane, chloroxylenol, ketoconazole, oxiconazole, butoconazole, clotrimazole, econazole, enilconazole, fenticonazole, miconazole, sulconazole, tioconazole, fluconazole, itraconazole, terconazole, active substances containing one or a plurality of cationic nitrogens such as cetyltrimethylammonium chloride, cetylpyridinium chloride, benzethonium chloride, diisobutylethoxyethyl-dimethylbenzylammonium chloride, diisobutyl-phenoxy-ethoxyethyl-dimethylbenzyl-ammonium chloride, N-alkyl-N,N-dimethyl-benzylammonium chloride, bromide, saccharinate, trimethylammonium chloride, sodium aluminium chlorohydroxylacetate, tricetylmethylammonium chloride, diaminoalkylamide, organic acids and the salts thereof, such as citric acid, unsaturated antimicrobial agents such as farnesol, terbinafine or naftifine, heterocyclic aromatic agents such as bifonazole, cloconazole, isoconazole, any other antimicrobial or antifungal agent known to those skilled in the art; and mixtures thereof.

—Thickeners:

Thickeners are present in the composition in a proportion ranging from 0.1% to 20% and preferably from 0.1% to 10% by weight with respect to the total weight of the composition.

The composition may also comprise thickening agents or rheology modifying agents, such as for example hydrophobically modified ethoxylated non-ionic urethanes, thickening polycarboxylic acids such as acrylates/steareth-20 methacrylate copolymer, carbomers, acrylate copolymers and acrylates/$C_{10}$-$C_{30}$ alkyl acrylate cross-polymer; natural gums and clays, modified clays such as bentones, metallic fatty acid salts such as aluminium stearates and hydrophobic silica; and mixtures thereof.

—pH adjusters:

The composition may also comprise acids and bases for adjusting the pH range of said composition. The bases may be mineral (sodium hydroxide, potash, ammonia) or organic such as mono-, di- or triethanolamine, aminomethylpropanediol, N-methyl-glucamine, basic amino acids such as arginine and lysine; and mixtures thereof.

The composition may further comprise one or a plurality of other ingredients such as pH buffers, vitamins, fragrances, and any other useful compound well known to those skilled in the art.

The following examples provide a non-limiting illustration of the present invention.

EXAMPLE

Composition for Skin

| Ingredients (INCI name) | Percentage |
|---|---|
| Water | q.s. 100% |
| Glycerine | 3 |
| Phenoxyethanol | 0.35 |
| $Na_2EDTA$ | 0.1 |
| Polyacrylate-13 and Polyisobutene and Polysorbate 20 & water | 1 |
| Glyceryl stearate and PEG-100 Stearate | 4 |
| Cetyl alcohol | 1 |
| Cyclopentasiloxane | 5 |
| Glyceryl tri-2-ethylhexanoate | 3 |
| Dicapryl carbonate | 2 |
| 2,3-dihydroxypropyl dodecanoate | 2 |
| Chlorophenesin | 0.27 |
| Polymethylacrylate | 2 |
| Fragrance | 0.1 |

Example 2

Composition for Hair

| 2,3-dihydroxypropyl dodecanoate | 1% |
|---|---|
| Sodium lauryl ether sulphate | 9% |
| Lauryl betaine | 2% |
| Magnesium sodium alkyl ether sulphate | 1% |
| PEG-18 Glyceryl oleate/cocoate | 1% |
| Polyquaternium 22 | 0.5% |
| NaCl | q.s. viscosity |
| Citric acid | q.s. pH |
| water | q.s. 100 g |

Example 3

Composition for Hair

| 2,3-dihydroxypropyl dodecanoate | 0.5% |
|---|---|
| Sodium lauryl ether sulphate | 9% |
| Cetrimonium chloride | 0.3% |
| Tween 20 | 5% |
| $Na_2EDTA$ | 0.2% |
| Thickener | 4% |
| NaCl | q.s. viscosity |
| Citric acid | q.s. pH |
| water | q.s. 100 g |

The invention claimed is:

1. A method of treating seborrhoea which comprises administering to a patient in need thereof a composition comprising:

a therapeutically effective amount of 2,3-dihydroxypropyl dodecanoate, and an adjuvant or excipient, wherein the 2,3-dihydroxypropyl dodecanoate is the sole anti-seborrheic active ingredient.

2. The method according to claim 1, characterised in that the seborrhoea is associated with the skin.

3. The method according to claim 1, characterised in that the seborrhoea is associated with the scalp.

4. A method for the cosmetic treatment of seborrhoea which comprises applying on skin or scalp an anti-seborrhoea composition comprising 2,3-dihydroxypropyl dodecanoate in a formulation for treating seborrhea, wherein the 2,3-dihydroxypropyl dodecanoate is the sole anti-seborrheic active ingredient.

* * * * *